United States Patent [19]

Roszinski et al.

[11] 4,354,983
[45] Oct. 19, 1982

[54] PROCESS FOR THE PURIFICATION OF O,O-DIALKYLTHIONOPHOSPHORIC ACID CHLORIDES

[75] Inventors: Hilmar Roszinski, Kendenich near Cologne; Heinz Harnisch, Lövenich near Cologne, both of Fed. Rep. of Germany

[73] Assignee: Hoechst Aktiengesellschaft, Hurth Knapsack, Fed. Rep. of Germany

[21] Appl. No.: 655,076

[22] Filed: Feb. 4, 1976

Related U.S. Application Data

[63] Continuation of Ser. No. 862,924, Oct. 1, 1969, abandoned.

[30] Foreign Application Priority Data

Oct. 5, 1968 [DE] Fed. Rep. of Germany ....... 1801432

[51] Int. Cl.$^3$ .............................................. C07F 9/20
[52] U.S. Cl. ..................................... 260/990; 260/986
[58] Field of Search .............................. 260/986, 990

[56] References Cited

U.S. PATENT DOCUMENTS 3,089,890  5/1963  Chupp et al. ................... 260/986 X
3,502,750  3/1970  Anglaret et al. .................... 260/986
3,794,703  2/1974  Beck et al. ........................... 260/990

*Primary Examiner*—Anton H. Sutto
*Attorney, Agent, or Firm*—Connolly and Hutz

[57] ABSTRACT

Production of O,O-dialkylthionophosphoric acid chlorides of the general formula:

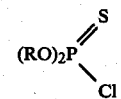

in which R is an alkyl radical having from 1 to 6 carbon atoms, by reacting a dialkyldithiophosphoric with chlorine. A reactor is supplied with O,O-dialkyldithiophosphoric acid and chlorine is added thereto at a temperature lower than about 75° C.; following completion of the chlorine addition, the reactor is supplied with a further portion of O,O-dialkyldithiophosphoric acid at a temperature between 0° and 75° C., and the resulting reaction mixture is distilled to isolate O,O-dialkylthionophosphoric acid chloride therefrom.

1 Claim, No Drawings

PROCESS FOR THE PURIFICATION OF O,O-DIALKYLTHIONOPHOSPHORIC ACID CHLORIDES

This application is a continuation of copending U.S. application Ser. No. 862,924, filed Oct. 1, 1969, entitled Process for the Manufacture of O,O-Dialkylthionophosphoric Acid Chlorides, now abandoned.

The present invention relates to a process for the manufacture of O,O-dialkylthionophosphoric acid chlorides of the general formula:

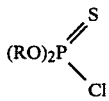

in which R is an alkyl radical having from 1 to 6 carbon atoms, by reacting a dialkyldithiophosphoric acid with chlorine.

It is known that O,O-dialkylthionophosphoric acid chlorides can be produced by processes comprising one or two steps. In all those cases in which chlorine gas is the chlorinating agent, it is customary to use 1.5 mols chlorine per mol O,O-dialkylthionophosphoric acid chloride. In addition thereto, the two-step processes give rise to the formation of disulfur dichloride, which is an undesirable secondary product. Some further processes are therefore carried out with the object of freeing the O,O-dialkylthionophosphoric acid chlorides from disulfur dichloride. The reason for this is that the two products can only incompletely be separated from one another by distillation.

The one-step process is illustrated by the following summation equation (I) and the two-step process by the following summation equations (II) and (III):

$$P_2S_5 + 4ROH + 3Cl_2 \rightarrow 2(RO)_2PSCl + 4HCl + 3S \qquad (I)$$

$$P_2S_5 + 4ROH \rightarrow 2(RO)_2P(S)SH + H_2S \qquad (II)$$

$$2(RO)_2P(S)SH + 3Cl_2 \rightarrow 2(RO)_2PSCl + 2HCl + S_2Cl_2 \qquad (III).$$

The present invention now unexpectedly provides a process for the manufacture of O,O-dialkylthionophosphoric acid chlorides which is easy to carry out and comprises supplying a reactor with O,O-dialkyldithiophosphoric acid, adding chlorine thereto at a temperature lower than 75° C. and, following completion of the chlorine addition, adding to the material in the reactor a further portion of O,O-dialkyldithiophosphoric acid at a temperature between 0° and 75° C., and distilling the resulting reaction mixture to isolate O,O-dialkylthionophosphoric acid chloride therefrom.

The distillation residue is preferably freed from precipitated sulfur and then used again as feed material for reaction of the O,O-dialkyldithiophosphoric acid with the chlorine.

The reaction should preferably be carried out using a solvent-free O,O-dialkyldithiophosphoric acid. It is also advantageous to use the feed material at the rate of substantially 1 mol O,O-dialkyldithiophosphoric acid per mol chlorine, for each reaction.

Following the introduction of 3 moles chlorine into 2 moles O,O-dialkyldithiophosphoric acid and reaction of these two compounds, a further mol O,O-dialkyldithiophosphoric acid should conveniently be added to the reaction product so obtained. This is done to obtain an O,O-dialkylthionophosphoric acid chloride free from disulfur dichloride as the final distillation product.

The final product should preferably be distilled off under vacuum and the O,O-dialkyldithiophosphoric acid, should be stirred under inert gas, preferably nitrogen, during the introduction of the chlorine thereinto.

The process of the present invention is most advantageously carried out supplying a reactor with about 2 mols O,O-dialkyldithiophosphoric acid; introducing 3 mols chlorine gas thereinto with agitation, under inert gas and while cooling the reaction product down to a temperature between 0° and 75° C. and, after completion of the chlorine addition, further cooling the reaction mixture down to room temperature; adding about one further mol O,O-dialkyldithiophosphoric acid and simultaneously cooling the reaction product to eliminate reaction heat set free and maintain the product at a temperature between 0° and 50° C.; and finally distilling the reaction product to isolate dialkylthionophosphoric acid chloride therefrom.

The fact that merely 1 mol chlorine gas is needed for the production of 1 mol O,O-dialkylthionophosphoric acid chloride is one of the advantages distinguishing the present process over prior art methods. The present process also enables very pure O,O-dialkylthionophosphoric acid chlorides completely free of disulfur dichloride to be obtained from chlorinated crude material, without any type of after-treatment. Furthermore, it is possible to carry out the present process in easy manner in the absence of any solvent and/or dispersing agent. This again is a considerable step forward in the art, seen under both technical and commercial aspects. The residue obtained substantially consists of sulfur. This is easy to remove from the sump material, which can readily be used again in further reactions. A still further advantage resides in the fact that the O,O-dialkylthionophosphoric acid chlorides are obtained in extremely high yields.

As shown in the following Examples, the reaction of the present invention takes the course illustrated by the following summation equation:

$$P_2S_5 + 4ROH + 2Cl_2 \rightarrow 2(RO)_2PSCl + 2HCl + 2S + H_2S \qquad (IV).$$

EXAMPLE 1

Production of O,O-dimethylthionophosphoric acid chloride

A relatively large quantity of O,O-dimethyldithiophosphoric acid for use in the chlorinating reaction was prepared from 222 grams (1 mol) phosphorus pentasulfide and 140 grams (10 weight percent excess) methyl alcohol. The phosphorus pentasulfide was added with agitation and under nitrogen as a protective gas to the alcohol. The reaction temperature was between 45° and 65° C. The overall reaction time including the time needed to expel residual hydrogen sulfide was about 3 hours. The 222 grams phosphorus pentasulfide gave 314 grams crude acid containing 79 weight percent O,O-dimethyldithiophosphoric acid, under the conditions specified.

314 grams of the crude acid were introduced into a reactor and chlorinated by adding thereto 2.4 mols chlorine gas, which was supplied within 2 hours, at about 50° C., with agitation, while cooling and under N₂ as a protective gas. Sulfur was found to separate after a period of about 1.75 hours and render the mixture turbid. Following completion of the chlorine addition, the reaction mixture was cooled down to room temperature and 157 grams crude O,O-dimethyldithiophosphoric acid were added dropwise thereto. The temperature increased to 30° C. The reaction mixture so produced was distilled in a column under a pressure of 14 mm mercury and at 64° C. to isolate O,O-dimethylthionophosphoric acid chloride, the column sump or base being maintained at a maximum temperature of 95° C. Sulfur which was still liquid was separated, following distillation. The remaining liquid sump or base material was allowed to remain in the reaction or distilling flask. 314 grams crude acid were added thereto, the whole was chlorinated in a manner analogous to that described above, and so on.

471 grams O,O-dimethyldithiophosphoric acid with a strength of 79 weight percent so treated were found to produce an average yield of 368 grams O,O-dimethylthionophosphoric acid chloride; this corresponded to a yield of 97.5 weight percent, based on the O,O-dialkyldithiophosphoric acid content of the crude acid. The product obtained was colorless, free of disulfur dichloride and very pure, as shown by gas chromatography.

EXAMPLE 2

Production of O,O-diethylthionophosphoric acid chloride

A relatively large quantity of O,O-diethyldithiophosphoric acid for use in the chlorinating reaction was prepared from 222 grams (1 mol) phosphorus pentasulfide and 202 grams (10 weight percent excess) ethyl alcohol. The phosphorus pentasulfide was added with agitation and under nitrogen as a protective gas to the alcohol. The reaction temperature was between 45° and 65° C. The overall reaction time including the time needed to expel evolved hydrogen sulfide was about 3 hours. The 222 grams phosphorus pentasulfide gave 382 grams crude acid containing 86 weight percent O,O-diethyldithiophosphoric acid, under the conditions specified.

382 grams of the crude acid were introduced into a reactor and chlorinated by adding thereto 2.6 mols chlorine gas, which was supplied within 2 hours, at about 50° C., with agitation, while cooling and under $N_2$ as a protective gas. Sulfur was found to separate after a period of about 1.75 hours and render the mixture turbid. Following completion of the chlorine addition, the reaction mixture was cooled down to room temperature and 191 grams crude O,O-diethyldithiophosphoric acid were added dropwise thereto. The temperature increased to 30° C. The reaction mixture so produced was distilled in a column under a pressure of 6 mm mercury and at 75° C. to isolate O,O-diethylthionophosphoric acid chloride, the column sump or base being maintained at a maximum temperature of 105° C. Sulfur which was still liquid was separated, following distillation. The remaining liquid sump or base material was allowed to remain in the reaction or distilling flask. 382 Grams crude acid were added thereto, the whole was chlorinated in a manner analogous to that described above, and so on.

573 grams O,O-diethyldithiophosphoric acid with a strength of 86 weight percent so treated were found to produce an average yield of 472 grams O,O-diethylthionophosphoric acid chloride; this corresponded to a yield of 94.4 weight percent, based on the O,O-diethyldithiophosphoric acid content of the crude acid. The product obtained was colorless, free of disulfur dichloride and very pure, as shown by gas chromatography.

We claim:

1. A process for the purification of a dialkylphosphorochloridothionate which comprises:
   (a) providing a mixture containing said phosphorochloridothionate and difficult to separate impurities containing sulfur, chlorine and phosphorus associated with the preparation of a dialkylphosphorochloroidothionate by the reaction of a chlorinating agent and a dialkylphosphorodithoic acid, selected from the group consisting of dimethyl and diethyl;
   (b) admixing and reacting with said mixture for a period of at least one minute at a temperature between about 0° C. and 75° C. a sufficient amount of said dialkylphosphorodithionic acid to react with at least one of the impurities therein to form more of the phosphorochloridothionate; and
   (c) separating and removing the phosphorochloridothionate in a substantially pure state from the impurities in the mixture.

* * * * *